Figure 1:
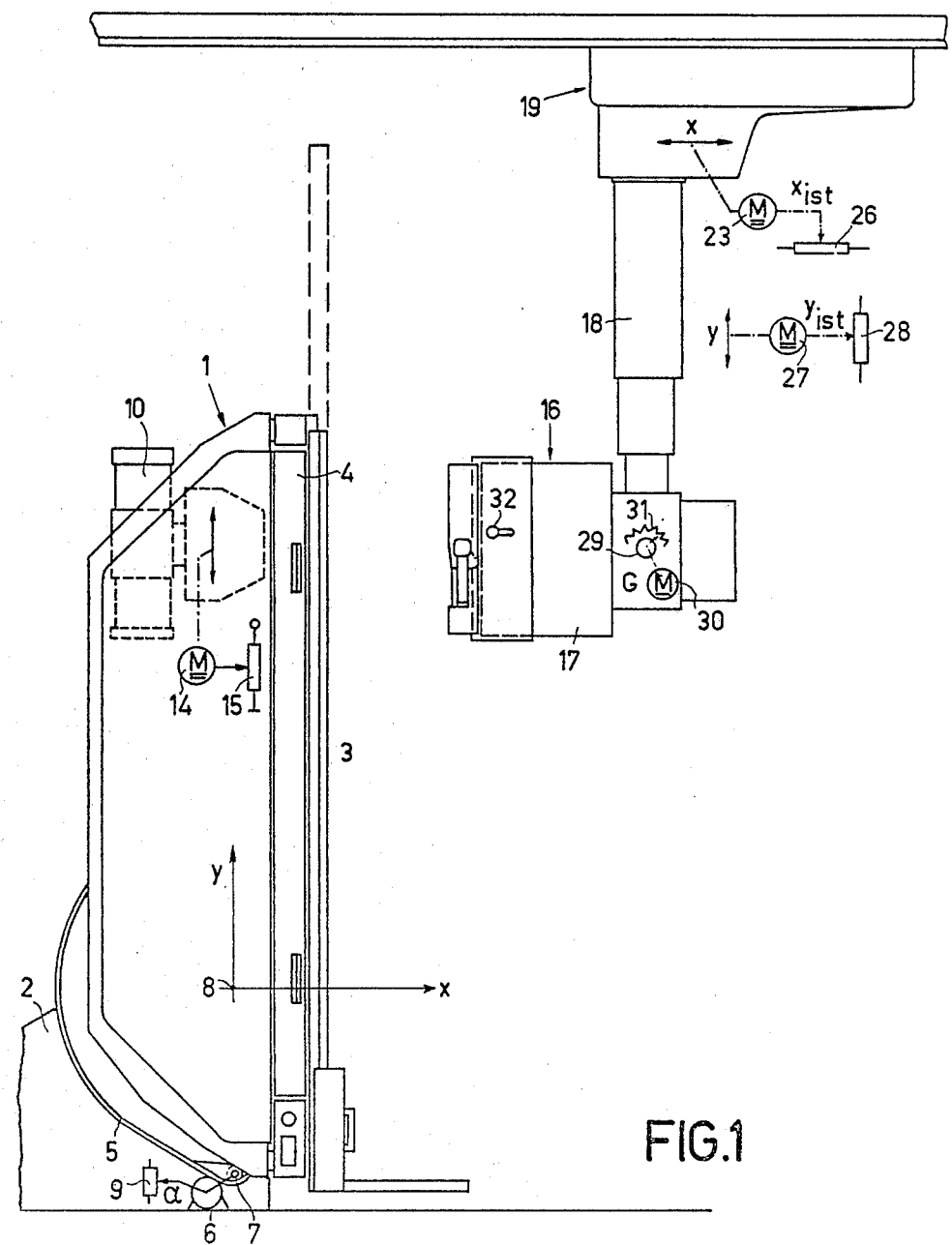

United States Patent [19]

Gieschen et al.

[11] 4,334,155
[45] Jun. 8, 1982

[54] X-RAY EXAMINATION APPARATUS, COMPRISING AN EXAMINATION TABLE WHICH CAN BE SWIVELLED AROUND A HORIZONTAL AXIS

[75] Inventors: Kurt Gieschen; Friedrich Reinger, both of Hamburg, Fed. Rep. of Germany

[73] Assignee: U.S. Philips Corporation, New York, N.Y.

[21] Appl. No.: 162,694

[22] Filed: Jun. 24, 1980

Related U.S. Application Data

[63] Continuation of Ser. No. 56,478, Jul. 11, 1979, abandoned.

[30] Foreign Application Priority Data

Jul. 14, 1978 [DE] Fed. Rep. of Germany ....... 2831058

[51] Int. Cl.³ .............................................. H05G 1/02
[52] U.S. Cl. .................................... 250/490; 250/525
[58] Field of Search ............... 250/447, 448, 454, 490, 250/525

[56] References Cited

U.S. PATENT DOCUMENTS 3,492,482  1/1970  Forsyth ............................. 250/490

*Primary Examiner*—Alfred E. Smith
*Assistant Examiner*—T. N. Grigsby
*Attorney, Agent, or Firm*—Jack E. Haken

[57] ABSTRACT

In an X-ray examination apparatus comprising an examination table which can be tilted around a horizontal shaft, a mechanical coupling between the X-ray source and the image section is replaced by a coupling between the table and the image section, the image intensifier being connected to a ceiling-mounted stand. Motors for vertical and horizontal displacement and rotation are provided. The three motors are controlled by an arithmetic device so that when the examination table is swivelled, the location and position of the image section with respect to the examination table is not changed. In an examination apparatus of this kind, the construction of the examination table may be substantially lighter, because the image section and the counterweights need not be supported by the examination table. The image section can be displaced in a larger area perpendicular to the top of the patient examination table and the patient can be introduced into the apparatus from the left as well as from the right.

6 Claims, 4 Drawing Figures

X-RAY EXAMINATION APPARATUS, COMPRISING AN EXAMINATION TABLE WHICH CAN BE SWIVELLED AROUND A HORIZONTAL AXIS

This is a continuation of application Ser. No. 056,478, filed July 11, 1979, now abandoned.

The invention relates to an X-ray examination apparatus, comprising an examination table which can be swivelled around a horizontal axis, an X-ray source which is displaceable parallel to the table top and perpendicularly to the swivel axis, an image detector which is directed onto the X-ray source in all swivel positions and which is situated on an opposite side end of the table top, and a first measuring device which supplies a first signal which is a measure for the inclination of the examination table.

An X-ray examination apparatus of this kind is known from German Offenlegungsschrift No. 22 00 848. Therein, the image detector, usually an X-ray image intensifier tube, is connected, by way of a bracket or a similar member, to a carriage which supports the X-ray source and which is arranged underneath the top of the examination table, said carriage being movable in the longitudinal direction of the table. The bracket prevents access to the image section from one side, so that the patient must always be brought into an examination position from an other side (the left side in the case of an upright examination apparatus).

The X-ray detector is then displaceable to only a limited extent in the direction transversely of the table top. This may give rise to the problem that the distance between the table top and the detector becomes too large for thick patient adjustment and too small for thin patient adjustment. Moreover, the distance between the focus and the patient is comparatively small in an X-ray examination apparatus of this kind, so that geometrical distortions are liable to occur and geometrical blurring caused by the finite dimensions of the focus may have a disturbing effect.

The known apparatus of this kind comprise a counterweight system, a counterweight being moved underneath the table top of the examination table in a direction which opposes that of the detector. In contemporary detectors, comprising an image intensifier, the mass of the detector and the counterweight may amount to some hundreds of kilogrammes. This mass must be displaced by the operator and must be swivelled together with the examination table. This necessitates a very stable construction of the examination table, for which generally a supporting leg must be provided on both sides of the table, the two legs being interconnected, underneath the table top, by way of a rigid system of rods. This construction no longer enables an increase of the distance between the X-ray source and the table top, because the displacement of the X-ray source in the longitudinal direction of the table top is impeded by this system of rods.

The invention has for its object to provide an X-ray examination device in which the construction of the examination table may be substantially lighter and in which the X-ray detector or the image converter can be displaced over a larger range transversely of the table top, while the access for the patient is free on both sides.

In order to achieve this object, an X-ray examination apparatus of the described kind in accordance with the invention is characterized in that the image detector or the X-ray source is mounted on a stand arrangement which is movable independently of the examination table and can be swivelled around an axis which is parallel with respect to the swivel axis, there being associated therewith a first drive motor which comprises a first control circuit for linking the inclination of this apparatus section to the inclination of the examination table, the device furthermore comprising a second and a third drive motor for displacement of said apparatus section in two mutually perpendicular directions which define a plane transversely of the swivel axis, a second and a third measuring device, each of which generates a signal which corresponds to the position or the displacement of the stand arrangement or of the apparatus section in the plane perpendicular to the swivel axis, at least one arithmetic unit which, during a swivelling movement of the examination table, continuously calculates, from the values of the three measuring devices which are measured in a preceding position of the table, the position or displacement of the apparatus section in a subsequent swivelled position, the orientation and the distance of the apparatus section with respect to the examination table then remaining unchanged, said arithmetic unit also serving for control of a second and a third control circuit which include the second and the third drive motor, respectively.

In the examination apparatus in accordance with the invention, therefore, there is no longer a rigid connection between the image detector and the X-ray source. As a result, the distance between the image detector and the X-ray source can be readily changed as desired. The patient then has access on both sides. The three measuring devices and the three position or displacement control circuits with the motor drives, controlled by the computer, enable the image detector to follow a swivelling movement of the examination table so as if it were mechanically connected thereto. The distance between the table top of the examination table and the image detector thus remains unchanged and a connecting line between the focus of the X-ray source and some other point on the image detector always intersects the table top in the same location. Therefore, when the examination table with the patient is swivelled around its axis, the zone irradiated by the radiation source and displayed by the image detector is not changed.

It is to be noted that German Offenlegungsschrift No. 27 11 358 already describes an X-ray examination apparatus in which an image converter is mounted on a stand arrangement and is movable thereon or therewith in two directions which extend perpendicularly with respect to each other and is rotatable around an axis extending perpendicularly to these two directions. The swivelling around this axis is automatically realized so that the image converter remains directed onto the X-ray source which is swivelled in synchronism. The examination table of this X-ray examination apparatus, however, cannot be swivelled, and the top thereof is always in the horizontal position, whilst the displacement of the image converter is realized exclusively by hand in both directions. Therefore, this X-ray examination apparatus is first of all intended for examinations of the coronary system. For stomach examinations, in which the patient must be swivelled into positions other than the horizontal position, this apparatus is not suitable.

The invention is suitable for use in examination apparatus in which the X-ray tube is situated underneath the table top (when the examination table occupies a horizontal position) and the image converter (image section) is mounted on the stand arrangement as well as in examination apparatus in which the X-ray source is situated above the table top (on the stand arrangement) and the image converter is situated underneath the table top (on a carriage which is movable in the longitudinal direction of the table). Particularly in apparatus of the latter kind a relative displacement between the radiation beam and the patient is possible in that the table top is moved in the longitudinal direction of the table and the frame supporting this top is moved perpendicularly to the table top. A displacement in the compression direction is possible in that the table top can be displaced perpendicularly with respect to its plane. A further embodiment of the invention which is better suitable for X-ray examination apparatus comprising an undertable tube is characterized in that the X-ray source is arranged underneath the top of the examination table and can be displaced in the longitudinal direction of the table by means of a fourth motor drive which is included in a fourth control circuit, the image converter mounted on the stand arrangement being displaceable by the user, the arithmetic device calculating, on the basis of the signals supplied by the second and the third measuring device, the displacement of the image converter in the longitudinal direction of the table, the value thus calculated serving as a reference value for the fourth control circuit.

For the stand arrangement, use could in principle be made of a floor stand comprising a horizontal, vertically displaceable supporting arm for the apparatus section, for example, the image converter (X-ray image section), said stand being horizontally displaceable on a floor rail by means of a motor drive. A floor stand of this kind, however, could also impede the free access for the patient. In a further embodiment of the invention, the stand arrangement comprises a ceiling-mounted stand which is horizontally displaceable by the second motor drive or by hand and which comprises a telescopic tube device which extends in the vertical direction and the lower end of which supports the image converter which can swivel around a shaft provided at that area, it being possible to extend and shorten said telescopic tube device by means of the third motor drive.

The invention will be described in detail hereinafter with reference to the accompanying diagrammatic drawing.

Figure 2:
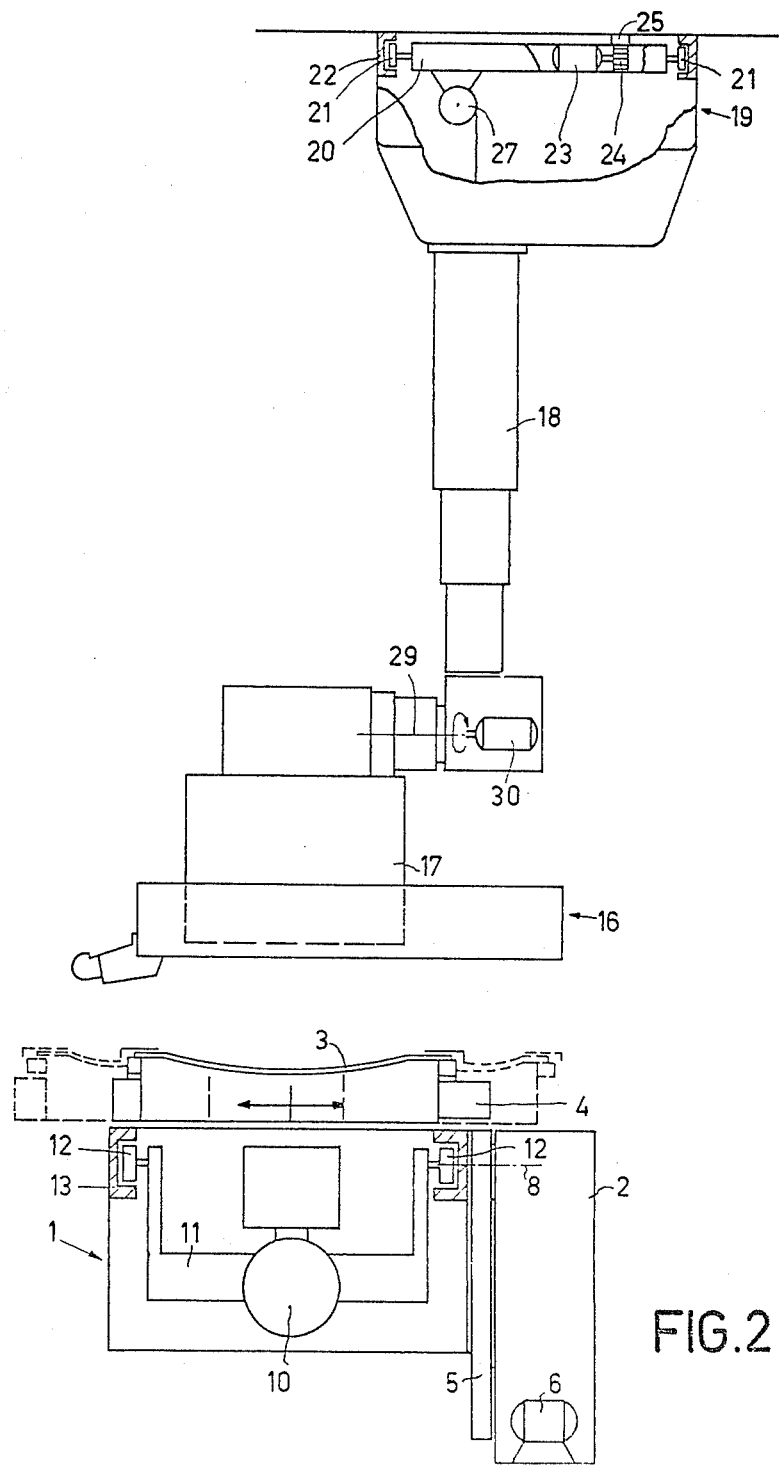
Figure 3:
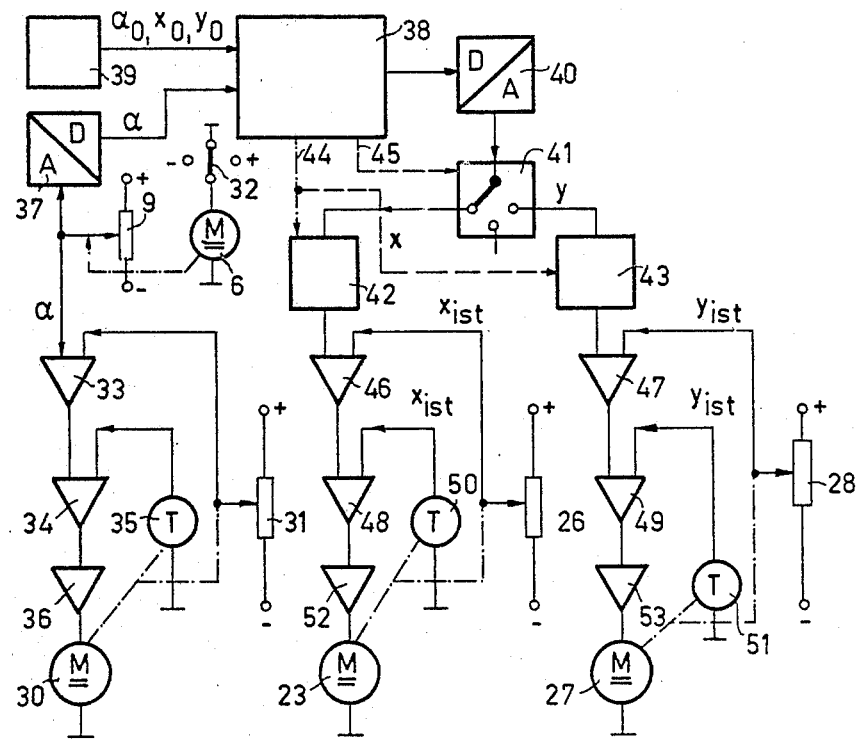
Figure 4:
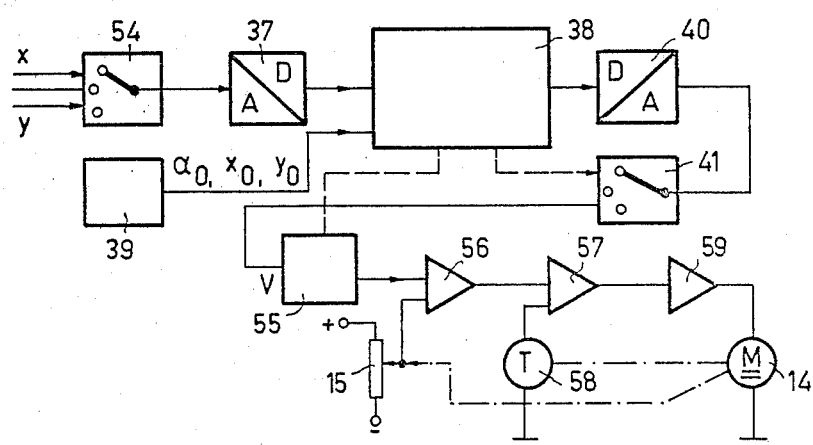

FIG. 1 shows an embodiment of an X-ray examination apparatus in accordance with the invention in the vertical position (side elevation), FIG. 2 shows the same X-ray examination apparatus in the horizontal position (viewed from the foot end), FIG. 3 shows a block diagram illustrating the control during a swivelling motion of the examination table, and FIG. 4 shows a block diagram illustrating the control during displacement of the image converter by the operator.

In the FIGS. 1 and 2, the reference numeral 1 denotes the examination table which comprises a base 2 which supports the device, a table top 3 and a frame 4 which is only roughly indicated. The frame 4 can be swivelled around a horizontal shaft 8 by means of a toothed segment 5 which is engaged by a pinion 7 which is driven by a diagrammatically indicated drive motor 6. The swivelling motion is measured by a transducer in the form of a potentiometer 9, the tapping of which is displaced by the drive motor 6, said potentiometer generating a signal which is proportional to the inclination of the table top with respect to the horizontal. During the swivelling motion, the frame 4 is uniformly displaced, i.e. towards the foot end, when the table top is swivelled from the vertical position shown in FIG. 1 into a horizontal position and further into a Tendelenburg position. As a result of this step, known from German Patent Specification No. 969 221, it is achieved that an apparatus of this kind can also be swivelled to the Tendelenburg position when the distance between the rotary shaft 8 and the floor amounts to less than half the length of the frame or the table top.

Underneath the table top 3 there is provided the X-ray source 10 which is supported by a carriage 11 (FIG. 2). The carriage 11 can roll on rails 13 by way of rollers 12, said rails being provided on the frame in a manner not shown and extending in the longitudinal direction of the table. For the displacement of the carriage 11 or the X-ray source 10, a direct current motor 14 (diagrammatically shown) is provided; this motor at the same time displaces the tapping of a potentiometer 15 so that the voltage derived therefrom corresponds to the position of the X-ray source or the carriage 11 in the longitudinal direction of the table.

The X-ray examination apparatus described thus far is substantially known. In the apparatus known thus far, however, the image converter or the X-ray image section is always mechanically connected to the X-ray source or to the carriage supporting this source, but in the apparatus in accordance with the invention no mechanical connection exists between these parts. Instead, the X-ray image section 16 of the apparatus in accordance with the invention, which can inter alia comprise an X-ray image intensifier 17, comprises a vertically extendable or retractable telescopic tube holder 18 which is secured on a ceiling-mounted stand 19. The ceiling-mounted stand 19 comprises a carriage 20 which can roll on rollers 21 in profiled rails 22 which are mounted against the ceiling and which extend horizontally and parallel with respect to the longitudinal direction of the table (in the horizontal position of the examination table). The carriage 20 can be displaced in the direction of the rails (x-direction) by means of a drive motor 23 which is connected to the carriage and which drives a gearwheel 24 which engages in a toothed rack 25 which is mounted against the ceiling parallel to the rails 22. The position of the carriage 20 is measured each time by means of a potentiometer 26, the tapping of which is coupled to the motor. The carriage furthermore supports a direct current motor 27 for moving the telescopic tube device 18 inwards and outwards in the vertical y-direction which extends perpendicularly to the direction of the rails. The position of the telescopic tube device, i.e. the distance between the image section 16 and the ceiling-mounted stand 19, can thus be changed by means of the drive motor 27 and can be measured by means of a potentiometer 28, the tapping of which can be displaced by the motor 27.

At the lower side of the telescopic tube device, the image section 16 is mounted so that it can swivel around a shaft 29 which is parallel to the shaft 8. For the swivelling of the image section around the shaft 29 there is provided a direct current motor 30, a potentiometer 31 measuring the angular position thereof or the inclination of the entrance display screen of the image section with respect to the horizontal.

The activities involved in the tilting of the examination table and the displacement of the image section will be described with reference to the FIGS. 3 and 4.

If the operator wishes to change the inclination of the examination table, the switch 32 provided on the image section 16 should be operated; one connection of the direct current motor 6 then receives a negative or positive potential, while the other connection is connected to ground. The motor subsequently starts to rotate in a direction which is dependent of the potential (negative or positive) whereto the one connection of the motor is connected via the switch 32; the pinion 7 then engages the toothed segment 5 and the supporting frame 4, together with the table top 3, the carriage 11 and the X-ray source 10, is swivelled around the shaft 8.

This method of control of the motor 6 does not allow the operator to determine the tilting speed. If this is necessary, for example, the motor 6 can be included in a speed or accelleration control circuit.

During the swivelling motion of the examination table, the tapping of the potentiometer 9 is displaced so that the voltage which can be constantly derived is proportional to the angle of inclination $\alpha$ of the table top 3 with respect to the horizontal. In a differential amplifier 33, this voltage is compared with the voltage on the tapping of the potentiometer 31 which is proportional to the angle of inclination of the image section 16. In a further differential amplifier 34, the difference thus obtained is compared with the direct voltage generated by a direct current tachogenerator 35 which is driven by the motor 30, the output signal which is proportional to the difference between the two voltages being applied to a power amplifier 36 which drives the motor 30, so that the X-ray image section 16 is swivelled around the shaft 29. The control circuit 30 . . . 36 thus forms a position control circuit which includes a speed control circuit, the adjusted value of the speed thereof being dependent of the control signal deviation on the inputs of the differential amplifier 33. It is thus achieved that the meter 30 operates at a low speed in the case of small deviations and at a high speed in the case of large deviations. If the voltage on the tapping of the potentiometer 31 corresponds substantially to the voltage on the tapping of the potentiometer 9, the motor 30 stops. The angle of inclination of the image section then corresponds to the angle of inclination of the table top of the examination table.

The voltage on the tapping of the potentiometer 9, that is to say the inclination $\alpha$ of the examination table, moreover, is converted, by means of an analog-to-digital converter 37, into a digital signal which is applied to the input of an arithmetic unit 38. From the angle of inclination $\alpha$, the arithmetic unit calculates the position x, y to be occupied by the shaft 29 in order to keep the distance of the image section 16 from and its position with respect to the table top 3 unchanged during the swivelling movement of the examination table in accordance with the equations $$x = x_0 \cos(\alpha - \alpha_0) + y_0 \sin(\alpha - \alpha_0) - b(\alpha - \alpha_0) \cos \alpha \quad (1)$$

$$y = -x_0 \sin(\alpha - \alpha_0) + y_0 \cos(\alpha - \alpha_0) + b(\alpha - \alpha_0) \sin \alpha \quad (2)$$

Therein, x is the distance between a perpendicular through the swivel shaft 29 and the swivel shaft 8, and y is the distance between a horizontal straight line through the swivel shaft 29 and the swivel shaft 8. $\alpha$ is the inclination of the table top with respect to the horizontal; thus, in the position shown in FIG. 1 $\alpha$ amounts to $+90°$ and decreases when the X-ray examination apparatus is swivelled counterclockwise. b takes into account the described displacement of the frame towards the foot end then occurring and is a constant factor which corresponds to the quotient from the displacement and the required swivelling of the apparatus. In the case of swivelling through $90°$, this factor may amount to, for example, 490 mm. $x_0$ and $y_0$ denote the coordinates of the swivel shaft 29 in a preceding angular position $\alpha_0$, for example, at the start of the swivelling movement. These values are applied from a memory 39 to the arithmetic device 38.

The equations (1) and (2) show that the movement to be performed by the swivelling shaft 29 in order to maintain the distance between the table top and the image sections constant and to prevent changing of the position of the image section with respect to the table top is dependent of the construction of the examination table. For example, if the supporting frame (and hence the table top) is not displaced during tilting around the shaft 8, the factor $b = 0$ and the swivel shaft 29 describes a circular path around the swivel shaft 8. Other table constructions do not comprise a fixed swivel shaft, but again an unambiguous relationship exists between the swivel angle of the examination table and the position of the swivel shaft 29 which can be analytically calculated.

As has already been stated, from the values $\alpha_0$, $x_0$, $y_0$, corresponding to the angular position of the examination table or the position of the swivel shaft 29 at the start of a swivelling movement and measured by means of the measuring value transducers 31, 26 and 28 and stored as a digital value in the memory 39, and from the swivel angle $\alpha$ measured in a subsequent angular position, the arithmetic device calculates the coordinates to be occupied by the swivel shaft 29 in order to prevent changing of the distance between the image section 16 and the table top 3 and of the position thereof with respect to each other during the swivelling movement. These values are successively calculated, after which the calculation is repeated for a new angular position $\alpha$. The values $\alpha_O$, $x_O$, $y_O$ can then be replaced by the new values. However, use can alternatively be made of the values $\alpha_O$, $x_O$ and $y_O$ present at the beginning of the swivelling movement. The new calculation of the values x and y can take place at periodic intervals or each time when the angle is changed by a given amount. The more often this calculation is performed, the more accurately the swivelling movement of the examination table will be followed by the image section 16.

The values x and y calculated by the arithmetic device 38 are applied in advance as reference values to position control circuits which comprise the motor drives 23 and 27. To this end, a digital-to-analog converter 40 is connected to the output of the arithmetic device 38, said converter converting the digital output signal of the arithmetic device 38 into an analog signal. Via a multiplexer 41, this analog signal is inter alia applied to the sample-and-hold circuits 42 and 43 which store the analog output signal of the digital-to-analog converter until the next x-value or v-value is calculated. The sample-and-hold circuits 42 and 43 and the multiplexer 41 are controlled by the arithmetic device 38 via the control lines 44 and 45, which are denoted by broken lines. Each of the output signals of the sample-and-hold circuits 42 and 43 serves as a reference value for a position control circuit which provides the displacement of the image sections 17 in the x and the y-direction, respectively.

The construction of the two position control circuits is identical. Therefore, only one of these circuits will be described herein and the relevant part of the other position control circuit is each time shown between brackets. The position reference value for the x (y) direction provided by the circuit 42 (43) is compared in a differential amplifier 46 (47) with the actual position value $x_{ist}$ ($y_{ist}$) which is derived for the potentiometer 26 (28), see FIG. 1. The control deviation serves as a reference value in a speed control circuit and is compared in a differential amplifier 48 (49) with an actual speed value $\dot{x}_{ist}$ ($\dot{y}_{ist}$) which is supplied by a direct current tachogenerator 50 (51) which is driven for the shifting in the x-direction and the y-direction, respectively, by the direct current motor 23 (27). The output signal of the differential amplifier 48 (49) which is proportional to the difference between the adjusted speed value and the actual speed value is applied to a power amplifier 52 (53) which operates the drive motor 23 (27) for the displacement of the apparatus section in the x-direction (y-direction) until the difference between the adjusted position value and the actual position value on the input of the differential amplifier 46 (47) is substantially zero.

The speed control underlying the position control ensures that in the case or large control deviations the relevant motor operates at a high speed and at a low speed in the case of small control deviations. The position control could also be realized by measuring, instead of the position (by the potentiometers 26 and 28), the speed or the time integral via the path. In that case, instead of the position values x and y, the arithmetic device should calculate the reference speed values or the reference values of the time integral via the path. These reference values are obtained by differentiation and integration (in the time), respectively, of the equations (1) and (2). Alternatively, the position and the speed can be simultaneously controlled. To this end, the differential amplifiers 46 and 48 (47 and 49) which each time form the control deviations must be connected in parallel (rather than consecutively). The reference speed value $\dot{x}_{ist}$ ($\dot{y}_{ist}$) each time associated with the positions x and y must then also be calculated by the arithmetic device 38. The reference speed values are obtained by differentiation in the time from the reference position values of the equations (1) and (2) in which the term to the right of the equality sign, the angle $\alpha$, is the only quantity which varies in the time. The control deviations thus determined independently or each other should be added and applied to the power amplifier 52 (53). The deviations from the desired path would in that case be very small.

As has already been stated, the arithmetic device 38 successively calculates the necessary reference values and repeats this calculation at given instants or each time when the inclination $\alpha$ changes by a given amount, the position control circuits then displacing the image section in accordance with the value each time newly calculated. The arithmetic device 38 may be a digital, suitably programmed small computer which includes a microprocessor.

If the operator displaces the image section with respect to the table top or the frame of the examination table in one of the known x-ray examination apparatus of the described kind, the carriage or the X-ray source automatically follows due to the mechanical coupling between the carriage supporting the X-ray source and the image section. In accordance with the invention, this is realized by means of a fourth control circuit. To this end (FIG. 4), the values x and y measured during a displacement by means of the transducers 26 and 28 are applied to the analog-to-digital converter 37, via a multiplexer 54 which can also be used to supply the measuring value corresponding to the angle of inclination $\alpha$ (FIG. 3). Therefrom, the arithmetic device calculates the position in which the X-ray source 10 is centred on the image section in accordance with the equation $$v = -x \cdot \cos \alpha_O + y \cdot \sin \alpha_O \qquad (3).$$

Therein, v is the distance between the central ray (that is to say, from the perpendicular to the focus of the X-ray source 10 on the table top (3)) and the swivel shaft 8. This value is more positive as the position of 10 is nearer to the head end of the table top. The value thus calculated is applied, via the digital-to-analog converter 40, the multiplexer 41 and a sample-and-hold circuit 55, to the fourth control circuit which may have a construction identical to that of the control circuits for the displacement of the X-ray image section in the x-direction and the y-direction. Thus, this control circuit comprises a first differential amplifier 56 in which the reference value supplied by the sample-and-hold circuit is compared with an actual position value derived from the potentiometer 15. The control deviation is compared by the differential amplifier 57 with a value which is supplied by the direct current tachogenerator 58 and which is proportional to the speed of displacement, the difference being amplified in a power amplifier 59 which controls the drive motor for the displacement of the tube carriage 11 in the longitudinal direction of the table for a period of time and in a direction such that the deviation of the signals on the output of the differential amplifier 56 is almost zero.

The displacement of the X-ray image section by hand can be realized only by the force exerted by the operator. For this it is assumed that a weightcompensation which is independent of the motor 27 is present (ceiling-mounted stands of this kind which comprise weight-compensation, for example, by means of a spring device, are already used in practice) and that the drive motors 23 and 27 are not in operation. This can be realized, for example, in that these motors are coupled to the apparatus section to be driven via a magnetic coupling (not shown), the coupling between the drive motor 23 or 27 and the apparatus section driven thereby being interrupted when the brakes for the X-ray image section are released.

The image section can alternatively be displaced by means of the motors 23 and 27. To this end it would be necessary to interrupt the control by the arithmetic device 38 and to supply the control circuits with, instead of the reference value calculated by the arithmetic device, a reference value which corresponds to a force exerted by the operator on a grip of the image section or on the image section itself in the x-direction and y-direction, and which could be generated by a transducer in the traction means for the x and for the y direction. Servomotor drives for the displacement of an X-ray image section of this kind are known, be it only in conjunction with a carriage which is coupled to the image section and which supports the X-ray source. The position of the switch 32 for the tilting of the examination table can be used as a criterion for the interruption of the control of the motor drives 23 and 27 by the arithmetic device: if the switch is activated, control is realized by the arithmetic device 38. In the other case, that is to say when the operator exerts a force on the image section or on a grip connected thereto, control is effected by the operator.

A further possibility of displacement of the image section by means of the motors 23 and 27 consists in the generating, by means of the grip of the image section, of a reference value for the displacement of the image section perpendicularly to the positioning table and parallel to the positioning top of the table, for example, as described in German Offenlegungsschrift No. 22 34 398. These reference values are applied in the described manner to the arithmetic device 38 which again calculates the reference values for the position control circuits of the motor drives 23 and 27 in dependence of the angle $\alpha$.

The measuring devices described thus far comprise measuring transducers in the form of potentiometers. These potentiometers each time supply a signal which is proportional to the position or the angular position. However, use can alternatively be made of measuring transducers which supply a signal which corresponds to the displacement of an apparatus section or to the swivelling (that is to say the changing of the angle of inclination during the tilting of the table) of the examination table or of the X-ray image section (inclement transducer). These transducers could be, for example, coding discs which are coupled each time to a motor drive and which generate a pulse each time in reaction to a displacement over a given distance or in reaction to a swivelling movement through a given angle. When those pulses are counted by a counter, the counter position each time corresponds to the position or the angular position when the pulses are added in the case of driving in the one direction and when they are subtracted when driving takes place in the opposite direction. For a given angle of inclination (for example, 90°, FIG. 1). or for a given position of the swivel shaft, the counter could be automatically adjusted to the value corresponding to this inclination in order to avoid drift phenomena. However, for the reference value, the displacement can be given in advance instead of the position or the swivelling can be given instead of the angle of inclination, in which case the control circuit for the displacement should comprise a corresponding transducer. The equation (3), for example, would then be $$\Delta v = v - v_0 = -(x - x_0) \cos \alpha_0 + (y - y_0) \sin \alpha_0 \quad (4)$$
$$= -\Delta x \cos \alpha_0 + \Delta_y \cdot \sin \alpha_0.$$

Referring to the block diagram of FIG. 4, first the angle of inclination $\alpha$ is determined and the arithmetic device 38 assigns the necessary reference values x and y to this angle of inclination. However, because the calculation time is finite and because the motor drives require a given period of time before the reference position or reference displacement is reached, each time a given lag occurs between the examination table and the X-ray image section. This could be prevented by adding or subtracting a small angular amount, for example 0.5° to or from the measured value $\alpha$, so that the amount of the angular variation is increased. As a result of such an increase of the angular position by the arithmetic device, it can be achieved that during the period of time required by the examination table for passing through the superposed angular amount (0.5°), the arithmetic device calculates the associated reference value which is adjusted by the control circuits, so that synchronism is substantially obtained. This procedure is possible in the device shown in FIG. 4.

It is in principle also possible to displace the ceiling-mounted stand in a horizontal direction which is perpendicular to the horizontal x-direction. In that case, the tube carriage must also be movable in the transverse direction and be adjustable by suitable follower control. The reference position of the tube carriage in this direction, however, corresponds to the position of the stand arrangement in this direction, so that the follower transport can be realized by means of a simple follower control system.

As is denoted by broken lines in FIG. 2, the table top may be movable transversely with respect to the longitudinal direction of the table. Moreover, the table top is also movable in known manner in the longitudinal direction of the table (denoted by broken lines in FIG. 1). Because the image section and any counterweights need not be supported by the examination table, the construction of this table may be substantially lighter. Therefore, as appears notably from FIG. 2, a single apparatus leg suffices. Thus, the X-ray source can in principle be mounted on the tube carriage so that it can be moved almost as far as the floor, perpendicularly to the patient examination top. Thus, a larger distance between the radiation source and the patient arises, which may be useful in allowing better observation of the details of an exposure thus made.

As has already been stated, the invention can also be used for apparatus in which the X-ray source is mounted above the examination table whilst the image section, usually an image intensifier, is mounted underneath the table. Often use is made of apparatus where after an examination by means of an undertable tube and an image section, a survey exposure is to be made by means of an X-ray tube arranged above the table. This is particularly simple in an X-ray examination apparatus in accordance with the invention, because the position of the X-ray image section is measured and can be stored. If the overtable X-ray source is mounted on a suitably constructed ceiling stand, it can be moved into the previously measured and stored position by suitable driving, like the ceiling-mounted stand 19, in the position previously occupied by the ceiling-mounted stand 19. A Bucky aperture situated underneath the table top can then be centred with respect to the overtable tube in the manner described for the X-ray source 10 with respect to the image section 16.

What is claimed is:

1. An X-ray examination apparatus comprising: an examination table (1) which is swivelable around a horizontal axis (8); an X-ray source (10) which is displaceable parallel to the top of the table (3) and perpendicularly to the swivel axis (8); an image detector (16) which is directed onto the X-ray source (10) in all swivel positions and which is situated on an opposite side of the table top (3) therefrom; and a first measuring device (9) which supplies a first signal which is a measure of the inclination of the examination table (1); characterized in that the apparatus includes stand arrangement means, an apparatus section which includes either the image detector (16) or the X-ray source (10) being mounted on the stand arrangement means (19) said apparatus section being movable independently of the examination table (1) and swivelable around an axis (29) which is parallel to the swivel axis (8), and further comprises: first drive motor means, (30) which comprises a first control circuit, which link the inclination of the apparatus section

(16) to the inclination of the examination table (1); second and third drive motor means (23, 27) which displace said apparatus section (16) in two mutually perpendicular directions which define a plane transversely of the swivel axis, and include, respectively, second and third measuring devices (26, 28), each of which generates a signal ($x_{ist}$, $y_{ist}$) which corresponds to the position or the displacement of the stand arrangement means (19) or of the apparatus section (16) in the plane perpendicular to the swivel axis (8); at least one arithmetic device (38) which, during a swivelling movement of the examination table (1), continuously calculates, from the signals ($\alpha_O$, $x_O$, $y_O$) generated by the three measuring devices (9, 26, 29) in a preceding position of the table, the position (x, y) or displacement of the apparatus section in a subsequent swivelled position ($\alpha$) and controls the first motor drive means therewith so that the orientation and the distance of the apparatus section (16) with respect to the examination table (1) remains unchanged, said arithmetic unit also controlling the second and the third drive motor means (23, 27).

2. An X-ray examination apparatus as claimed in claim 1, characterized in that the X-ray source (10) is mounted underneath the table top (3) of the examination table and is movable; and further comprising fourth motor drive means which move the source in the longitudinal direction of the table, the image detector (16) being movably mounted on the stand arrangement means (19); and wherein the arithmetic unit (38) calculates the position or the displacement of the image detector in the longitudinal direction of the table from the signals then supplied by the second and the third measuring device (26, 29), the value (v) thus calculated serving as a reference value for the fourth motor drive means.

3. An X-ray examination apparatus as claimed in claim 1, characterized in that the stand arrangement means comprises a ceiling-mounted stand (19) which is horizontally movable by the second motor drive means (23) and which comprises a vertically extending telescopic tube device (18) whose lower end swivelably supports the image detector (16) the third motor drive means functioning to effect extension and retraction of said telescopic device (27).

4. An X-ray examination apparatus as claimed in claim 1, characterized in that the first, the second and the third measuring device form part of the first, the second and the third drive means, respectively.

5. An X-ray examination apparatus as claimed in claim 4, characterized in that the values (x, y) calculated by the arithmetic unit (38) serve as reference values for the second and the third drive means which compare the reference value with the signal ($x_{ist}$, $y_{ist}$) supplied by the second and the third measuring device, respectively, and which control the difference to a minimum value.

6. An X-ray examination apparatus as claimed in claim 1, characterized in that the signal ($\alpha$) corresponding to the next angular position of the examination table (1) serves as a reference value for the first motor drive means (30).

* * * * *